United States Patent
Choi et al.

(10) Patent No.: US 11,484,484 B2
(45) Date of Patent: Nov. 1, 2022

(54) COMPOSITION FOR ALLEVIATING SKIN BARRIER DYSFUNCTION

(71) Applicant: LG HOUSEHOLD & HEALTH CARE LTD., Seoul (KR)

(72) Inventors: Seonguk Choi, Seoul (KR); Mi Sun Kim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 17/042,653

(22) PCT Filed: Mar. 29, 2019

(86) PCT No.: PCT/KR2019/003752
§ 371 (c)(1),
(2) Date: Sep. 28, 2020

(87) PCT Pub. No.: WO2019/190290
PCT Pub. Date: Oct. 3, 2019

(65) Prior Publication Data
US 2021/0022976 A1 Jan. 28, 2021

(30) Foreign Application Priority Data
Mar. 29, 2018 (KR) .................. 10-2018-0036845

(51) Int. Cl.
*A61K 8/365* (2006.01)
*A61K 8/37* (2006.01)
(Continued)

(52) U.S. Cl.
CPC ............ *A61K 8/365* (2013.01); *A61K 8/37* (2013.01); *A61K 8/44* (2013.01); *A61K 31/192* (2013.01);
(Continued)

(58) Field of Classification Search
None
See application file for complete search history.

(56) References Cited

U.S. PATENT DOCUMENTS

| | | |
|---|---|---|
| 2004/0044077 A1 | 3/2004 | Katagiri et al. |
| 2008/0095866 A1 | 4/2008 | Declercq et al. |
| 2014/0023602 A1 | 1/2014 | Tanaka et al. |

FOREIGN PATENT DOCUMENTS

| | | |
|---|---|---|
| KR | 10-2003-0074690 A | 9/2003 |
| KR | 10-2010-0085435 A | 7/2010 |

(Continued)

OTHER PUBLICATIONS

Liebert, "Final Report on the Safety Assessment of Amyl Acetate and Isoamyl Acetate," Journal of the American College of Toxicology, vol. 7, No. 6, 1988. pp. 706-719; (Year: 1988).*

(Continued)

*Primary Examiner* — Kyung S Chang
(74) *Attorney, Agent, or Firm* — Birch, Stewart, Kolasch & Birch, LLP

(57) ABSTRACT

A cosmetic composition for alleviating skin barrier dysfunction, a pharmaceutical composition for preventing or treating skin barrier dysfunction, a quasi-drug composition for preventing or alleviating skin barrier dysfunction, a method for alleviating skin barrier dysfunction, and a method for preventing or treating skin barrier dysfunction. Hydroxycinnamic acid, isoamyl acetate, or betaine promotes autophagic activity independently of the mTOR pathway in keratinocytes and accelerates the turnover of the epidermis to increase the thickness of the epidermis, thereby improving the barrier function and preventing the senescence-induced attenuation of the epidermis.

6 Claims, 5 Drawing Sheets

(51) Int. Cl.
  A61K 8/44    (2006.01)
  A61K 31/192  (2006.01)
  A61K 31/205  (2006.01)
  A61K 31/22   (2006.01)
  A61Q 9/00    (2006.01)
  A61Q 19/08   (2006.01)
(52) U.S. Cl.
  CPC ............ *A61K 31/205* (2013.01); *A61K 31/22* (2013.01); *A61Q 19/08* (2013.01)

(56) References Cited

FOREIGN PATENT DOCUMENTS

KR    10-2015-0043026 A    4/2015
KR    10-2015-0043028 A    4/2015

OTHER PUBLICATIONS

Akinduro et al., "Constitutive Autophagy and Nucleophagy during Epidermal Differentiation", Journal of Investigative Dermatology (2016), vol. 136, pp. 1460-1470. (Year: 2016).*

Sreenivas, "what to know about your skin barrier and how to protect it", WebMD, retrieved from on-line website: https://www.webmd.com/skin-problems-and-treatments/skin-barrier-what-to-know, last visit Dec. 15, 2021). (Year: 2021).*

Sullivan et al., "Xerosis Cutis", [(retrieved from on-line website: www.healthline.com/health/xerosis, 2018, pp. 1-9)]. (Year: 2018).*

Bian et al., "Ferulic Acid Induces Mammalian Target of Rapamycin Inactivation in Cultured Mammalian Cells," Biol. Pharm. Bull., vol. 36, No. 1, Jan. 2013, pp. 120-124.

International Search Report (PCT/ISA/210) Issued in PCT/KR2019/003752, dated Jul. 10, 2019.

Taofiq et al., "Hydroxycinnamic Acids and Their Derivatives: Cosmeceutical Significance, Challenges and Future Perspectives, a Review," molecules, vol. 22, No. 281, pp. 1-24.

Extended European Search Report for European Application No. 19777953.1, dated Feb. 7, 2022.

Lorencini et al., "Active ingredients against human epidermal aging," Ageing Research Reviews, vol. 15, 2014 (published online Mar. 25, 2014), pp. 100-115 (16 pages total).

Mintel, "Hair & Body Oil," Database GNPD [Online], Accession No. 5458809, Feb. 2018, pp. 1-3 (3 pages total).

Nichols et al., "Skin photoprotection by natural polyphenols: anti-inflammatory, antioxidant and DNA repair mechanisms," Arch Dermatol Res, vol. 302, 2010 (published online Nov. 7, 2009), pp. 71-83 (13 pages total).

Seo et al., "Effects of p-coumaric acid on erythema and pigmentation of human skin exposed to ultraviolet radiation," Clinical and Experimental Dermatology, vol. 36, 2010, pp. 260-266 (7 pages total).

\* cited by examiner

[FIG. 1]
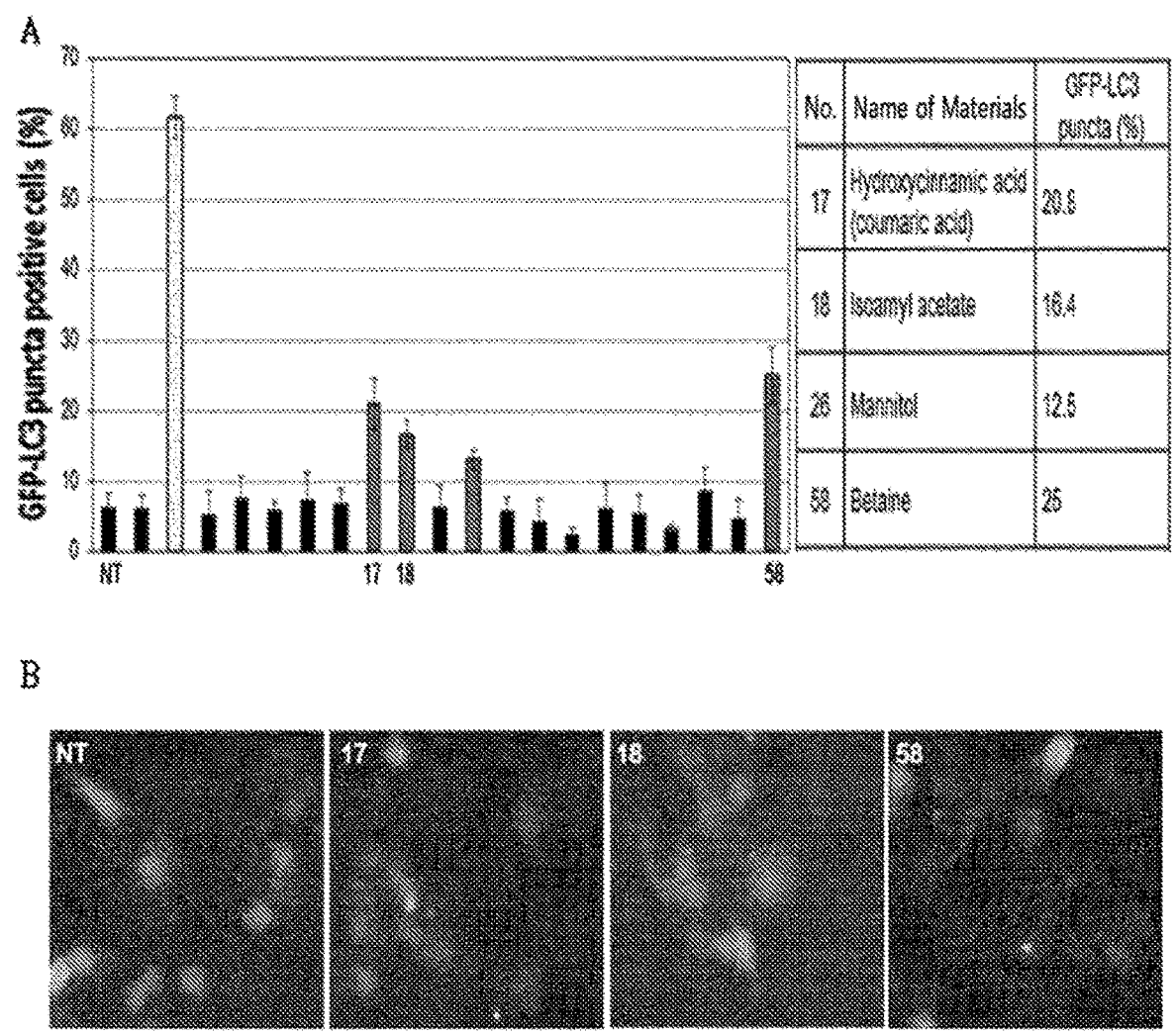

[FIG. 2]
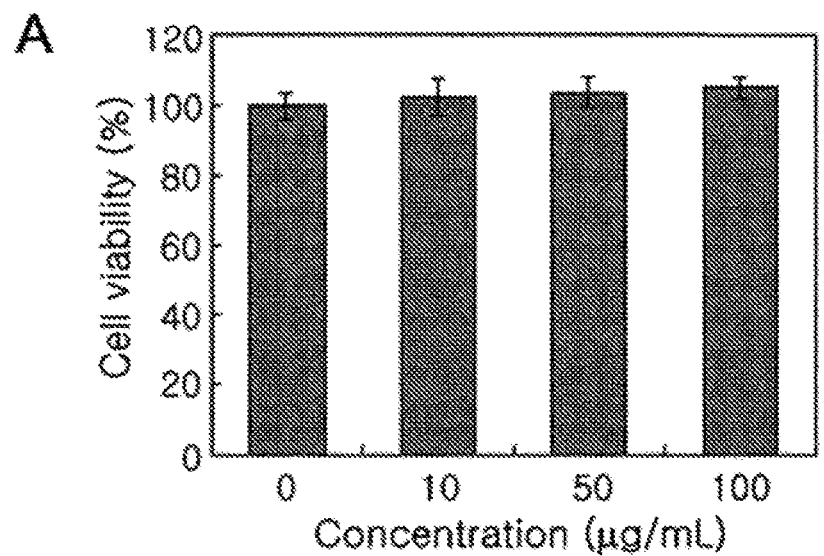
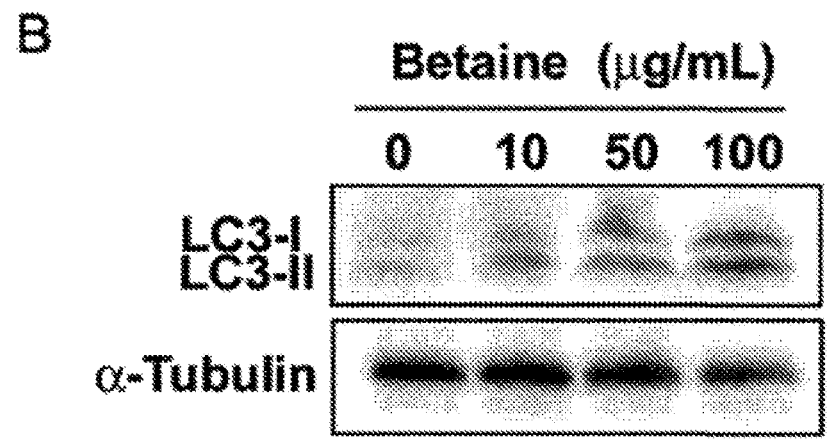
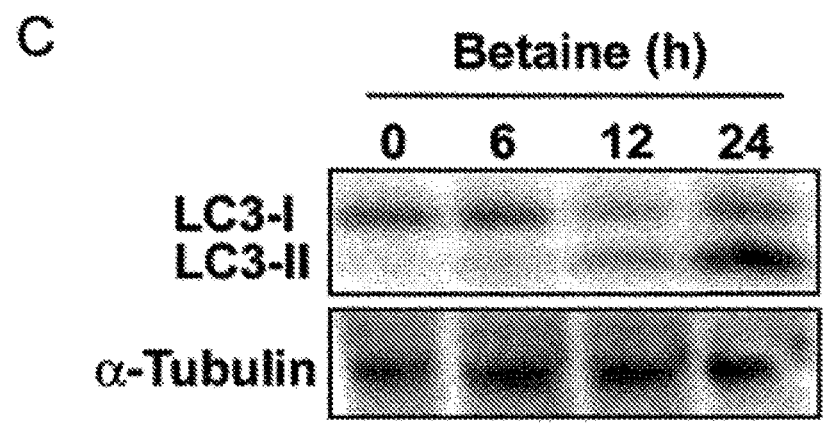

[FIG. 3]
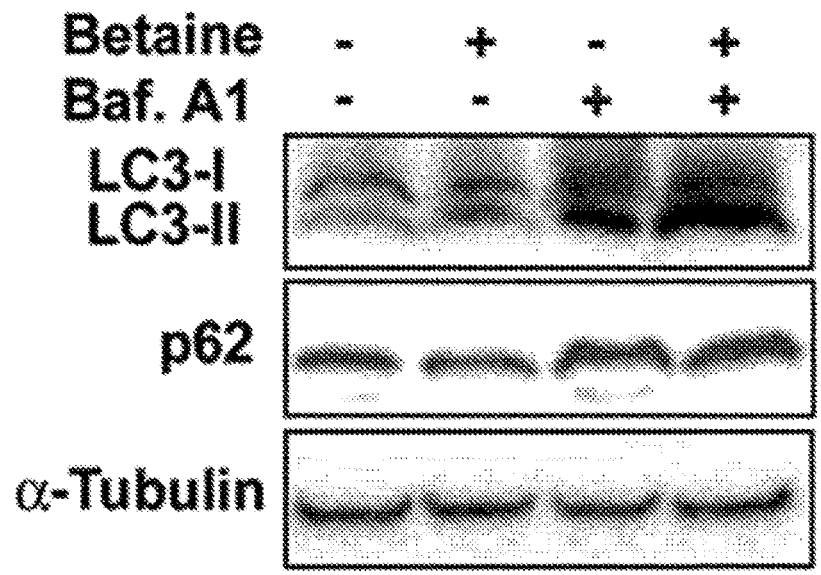
[FIG. 4]
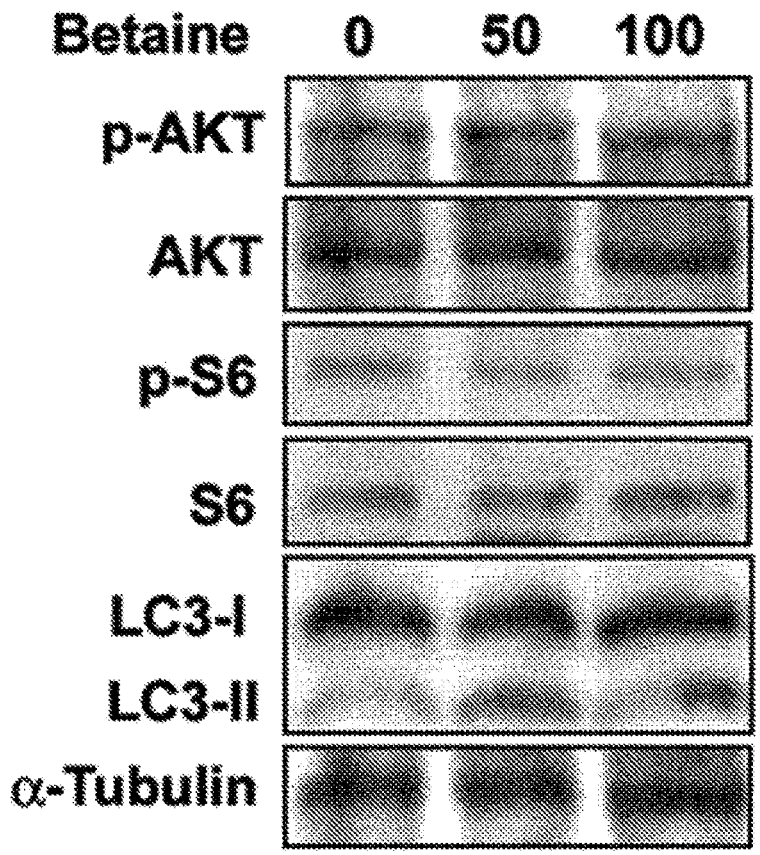

[FIG. 5a]
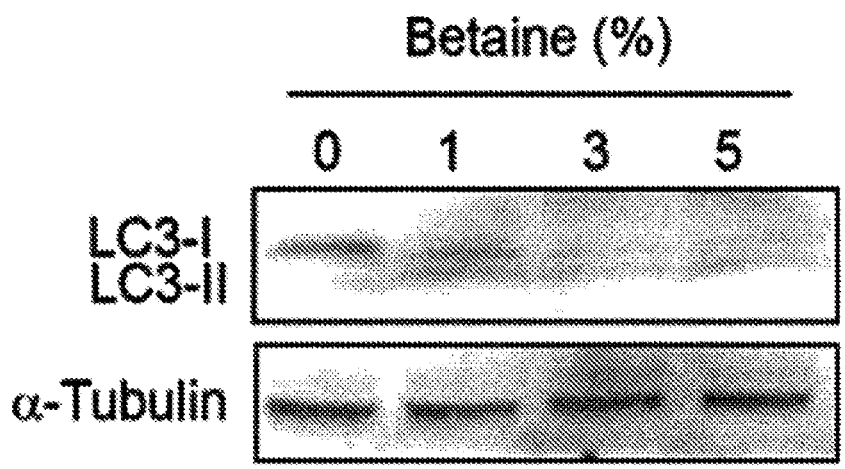
[FIG. 5b]
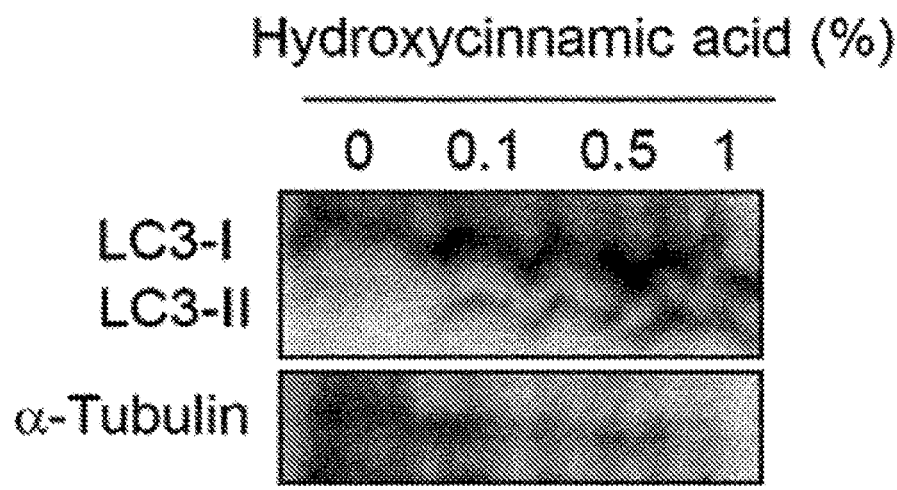

[FIG. 5c]
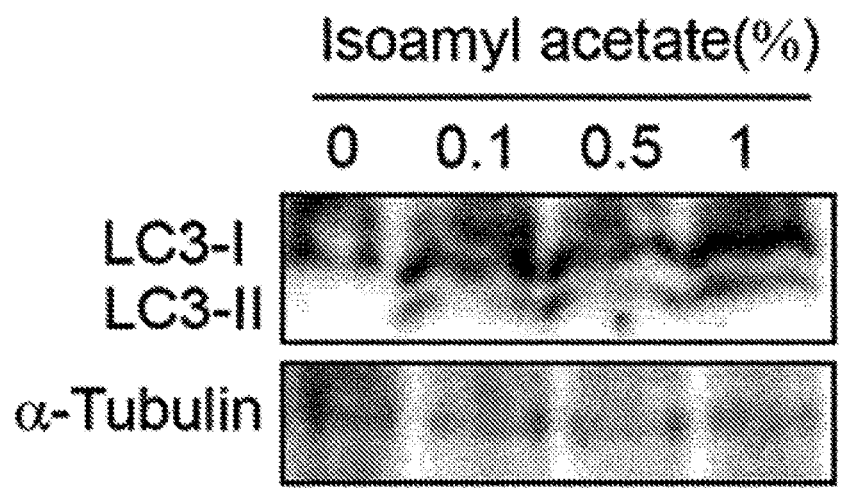
[FIG. 5d]
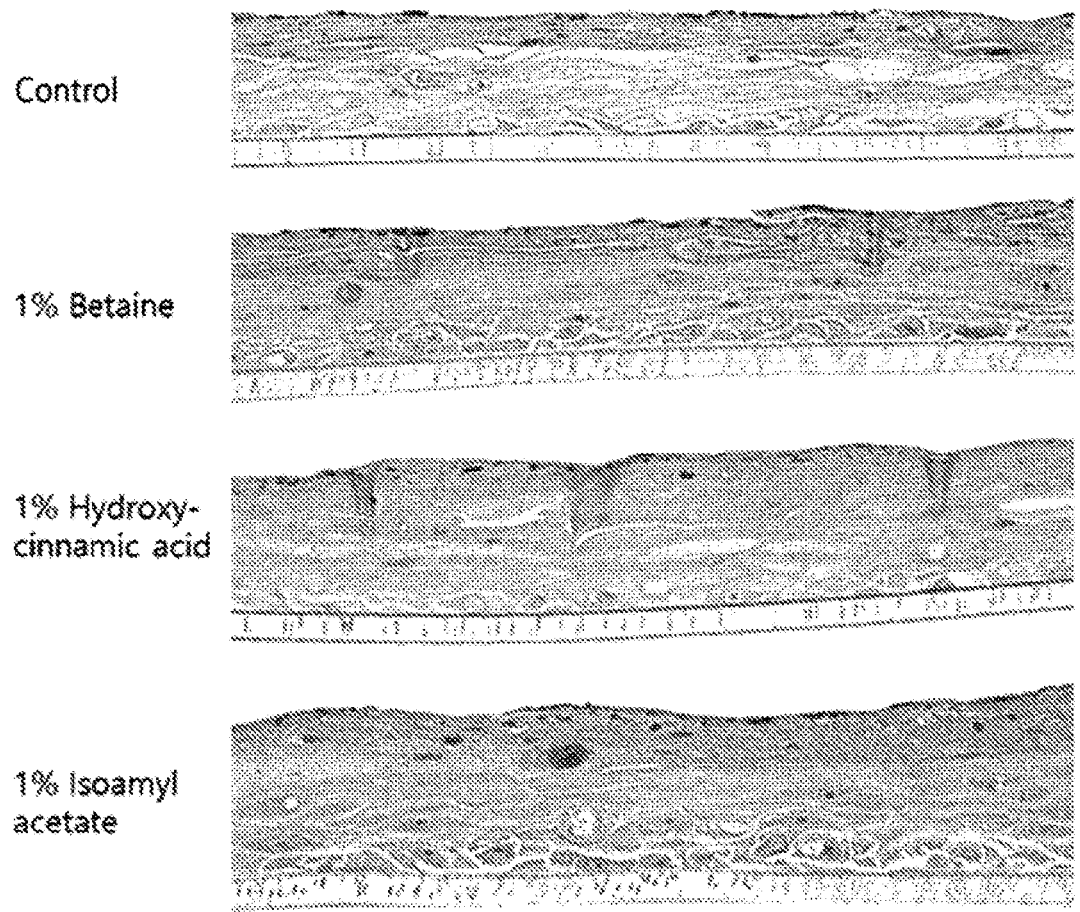

COMPOSITION FOR ALLEVIATING SKIN BARRIER DYSFUNCTION

TECHNICAL FIELD

The present invention relates to a cosmetic composition for alleviating skin barrier dysfunction, a pharmaceutical composition for preventing or treating skin barrier dysfunction, a quasi-drug composition for preventing or alleviating skin barrier dysfunction, a method for alleviating skin barrier dysfunction, and a method for preventing or treating skin barrier dysfunction.

BACKGROUND ART

The epidermis is tissue that is always in contact with the external environment. It mainly protects the human body from external physical damage and chemical substances, prevents bacteria, fungi, and viruses from invading the skin, and has a role as a protective barrier to prevent moisture loss. The epidermis is composed of the stratum basale, stratum spinosum, stratum granulosum, and stratum corneum, which is the outermost layer. Although the stratum corneum is shed and falls off gradually, the keratinocytes located in the basement membrane divide asymmetrically and differentiate in the direction toward the outside of the epidermis to maintain the structural and functional homeostasis of the epidermis. In recent years, the increase in the exposure to strong ultraviolet rays due to environmental pollution, etc., as well as inflammatory reactions due to fine dust, attenuation of the barrier function, and the increase of moisture loss in the skin resulting therefrom have led to the acceleration of skin aging and the increase in skin damage and incidence rate of related diseases (KR 10-2015-0043026 A).

Autophagy is a mechanism by which the damaged substances are removed and energy is regenerated by degradation of old or damaged intracellular substances and organelles when the intracellular stress factor is excessively generated or the intracellular energy source is depleted, and autophagic activity has been observed in the epidermis as well as in several epithelial tissues. According to various reports, autophagy is essential for maintaining the homeostasis of the epidermis and exerting appropriate skin barrier function. In particular, it plays an important role in a viral infection of the epidermis, inflammatory reaction due to ultraviolet rays, melanosome delivery, and differentiation of keratinocytes, and also has a crucial role in removing mitochondria, Golgi apparatus, vesicles, nuclei, etc. when the keratinocytes finally differentiate into the stratum corneum. As aging progresses or accelerates, it has been reported in various recent studies that intracellular autophagic activity decreases rapidly. If autophagy is suppressed, aged mitochondria or proteins with denatured structures accumulate excessively in the cell, leading to an increase in intracellular free radicals and oxidative stress, thereby increasing cell death and accelerating aging.

Light Chain 3 (LC3) are proteins whose amount increases during autophagy. They undergo a post-translational transformation process during the autophagy process. After translation into Pro-LC3, they produce cytoplasmic LC3-I through cleavage of the $22^{nd}$ amino acid at the carboxy terminal by autophagy-related protein 4 (atg4), and during autophagy, LC3-I is converted to LC3-II, while being lipidated by phosphatidylethanolamine (PE) through a ubiquitin-like system involving atg3 and atg7, and consequently, LC3 is linked to autophagosomes.

Mammalian target of rapamycin (mTOR) is a ser/thr kinase, which responds to changes in ATP and amino acids and is known to have a role in balancing the availability of nutrients and cell growth. In an environment where sufficient nutrients can be supplied, mTOR is phosphorylated through the class I PI3K/Akt signaling pathway and then transmits a positive signal to the p70S6 kinase, and is involved in the inactivation of 4E-BP1 (i.e., an eIF4E inhibitor) to translate specific mRNA groups, and also inhibits autophagy.

DISCLOSURE

Technical Problem

According to the present invention, in order to improve the barrier function by promoting epidermal differentiation through activation of autophagy, which is reduced by aging or external stimuli, an extensive search has been conducted starting from a library of single compounds derived from natural substances for those that promote autophagic activity of keratinocytes, and as a result, hydroxycinnamic acid, isoamyl acetate, and betaine have been found to be appropriate. Additionally, the present invention has been completed by confirming the efficacy of promoting autophagic activity and increasing the thickness of the epidermis in a 3D artificial skin model based on an in vitro experiment.

Technical Solution

One object of the present invention is to provide a cosmetic composition for alleviating skin barrier dysfunction, including one or more compounds selected from the group consisting of hydroxycinnamic acid, isoamyl acetate, and betaine, or an acceptable salt thereof, as an active ingredient.

Another object of the present invention is to provide a pharmaceutical composition for preventing or treating skin barrier dysfunction, including one or more compounds selected from the group consisting of hydroxycinnamic acid, isoamyl acetate, and betaine, or a pharmaceutically acceptable salt thereof, as an active ingredient.

Still another object of the present invention is to provide a quasi-drug composition for preventing or alleviating skin barrier dysfunction, including one or more compounds selected from the group consisting of hydroxycinnamic acid, isoamyl acetate, and betaine, or a pharmaceutically acceptable salt thereof, as an active ingredient.

Still another object of the present invention is to provide a method for alleviating skin barrier dysfunction, including applying the cosmetic composition to a subject.

Still another object of the present invention is to provide a method for preventing or treating skin barrier dysfunction, including administering the pharmaceutical composition to a subject excluding humans, or applying the pharmaceutical composition to the skin of a subject excluding humans.

Advantageous Effects

According to the present invention, hydroxycinnamic acid, isoamyl acetate, or betaine promotes autophagic activity independently of the mTOR pathway in keratinocytes and accelerates the turnover of the epidermis to increase the thickness of the epidermis, thereby improving the barrier function and preventing the senescence-induced attenuation of the epidermis.

BRIEF DESCRIPTION OF DRAWINGS

FIG. 1 is the result of screening materials for activating autophagy in keratinocytes. Specifically, FIG. 1A shows the results of comparing the number of cells with increased GFP-LC3 puncta vesicles in the cytoplasm in a library of single compounds derived from various natural substances.

FIG. 1B shows the observation results under a fluorescence microscope according to no treatment (NT), and treatment with hydroxycinnamic acid, isoamyl acetate, or betaine for HaCaT cells introduced with the GFP-LC3 vector.

FIG. 2 is the result of confirming whether cytotoxicity and autophagy are promoted by betaine in keratinocytes.

Specifically, FIG. 2A confirms the cytotoxicity according to the treatment of each concentration of betaine, and FIG. 2B shows the increase of LC3-II according to the treatment of each concentration/time of betaine.

FIG. 3 shows the experimental results of confirming the mechanism by which autophagosomes are increased by betaine.

FIG. 4 shows the experimental results of confirming the mechanism of activation of mTOR pathway—independent autophagy.

FIG. 5 is the result of confirming the effect of promoting differentiation in the epidermis and whether the thickness of the epidermis increases in a 3D artificial skin model. Specifically, FIGS. 5a, 5b, and 5c show the results of confirming whether autophagy is promoted by treating with hydroxycinnamic acid, isoamyl acetate, or betaine of cream formulations at each concentration in a 3D artificial skin model, and FIG. 5d shows the results of confirming the increase in epidermal thickness.

BEST MODE FOR CARRYING OUT THE INVENTION

The present invention will be described in detail as follows. Meanwhile, respective descriptions and embodiments disclosed herein may also be applied to other descriptions and embodiments. That is, all combinations of various elements disclosed herein fall within the scope of the present invention. Further, the scope of the present invention is not limited by the specific description below.

In order to achieve the objects above, one aspect of the present invention provides a cosmetic composition for alleviating skin barrier dysfunction, including one or more compounds selected from the group consisting of hydroxycinnamic acid, isoamyl acetate, and betaine, or an acceptable salt thereof, as an active ingredient. The cosmetic composition may include a combination of two or more compounds selected from the group consisting of hydroxycinnamic acid, isoamyl acetate, and betaine, but is not limited thereto.

The one or more compounds selected from the group consisting of hydroxycinnamic acid, isoamyl acetate, and betaine, or an acceptable salt thereof, included in the cosmetic composition may promote autophagic activity in keratinocytes and accelerate the turnover of the epidermis to increase the thickness of the epidermis, thereby improving the barrier function and preventing the senescence-induced attenuation of the epidermis.

In one Experimental Example of the present invention, candidate compounds expected to promote autophagy were treated to HaCaT cells introduced with the GFP-LC3 vector, and then the number of cells with increased GFP-LC3 puncta vesicles was compared in each cell. As a result, it was confirmed that when the cells were treated with hydroxycinnamic acid, isoamyl acetate, and betaine, the proportions of cells with increased GFP-LC3 puncta vesicles were 20.8%, 16.4%, and 25%, respectively, which were significantly higher than those for other compounds. From the results, it was confirmed that the one or more compounds selected from the group consisting of hydroxycinnamic acid, isoamyl acetate, and betaine, or an acceptable salt thereof, can be used as a compound material for activating autophagy in keratinocytes and improving skin barrier function.

As used herein, the term "hydroxycinnamic acid $(C_9H_8O_3)$" refers to coumaric acid (i.e., trans-hydroxycinnamic acid) or coumarinic acid (i.e., cis-hydroxycinnamic acid) depending on its isomeric form. The native type thereof refers to the trans form of coumaric acid. Coumaric acid has a more stable form than coumarinic acid and has colorless, needle-shaped crystals. It is well soluble in hot water and ethanol, and has a melting point of 208° C.

As used herein, the term "isoamyl acetate $(C_7Hl_4O_2)$" is also referred to as isopentyl acetate, and is known as a banana-scented fragrance in the form of a transparent liquid. It is not well soluble in water, but soluble in alcohol and organic solvents, and has a specific gravity of 0.868 to 0.878 and a boiling point of 142° C.

As used herein, the term "betaine" refers to trimethylglycine (TMG) with the formula of $C_5H_{11}NO_2$, and is synthesized through the irreversible oxidation process of choline in the mitochondria in vivo. Betaine is essential for the synthesis of methionine because it transfers the methyl group bound to the nitrogen atom of glycine, and thus is widely used as a supplement for methionine, the intake of which is low in general dietary habits. Additionally, betaine has the effect of reducing eye and skin irritation and has a unique zwitterionic electromagnetic property.

As used herein, the term "skin" refers to the tissue covering the body surface of an animal. It may be used in a very inclusive sense to include the scalp and hair in addition to the tissue covering the surface of the face or body. Meanwhile, in the present specification, the skin may include not only the skin of the living body, but also artificial skin or a skin mimic that realizes the state of the skin of the living body.

As used herein, the term "skin barrier function" refers to all functions of the skin, particularly the stratum corneum of the epidermis acting as a barrier layer from the outside, such as preventing moisture leakage to the outside and controlling the access of substances from the outside, but is not limited thereto.

As used herein, the term "skin barrier dysfunction" refers not only to a condition in which the skin barrier function is deteriorated or damaged, but also to a condition in which the skin barrier function is likely to be deteriorated or damaged, and all conditions that need to prevent the above conditions, but is not limited by the specific type or severity of symptoms. More specifically, the skin barrier dysfunction may include all of, but is not limited to, an inflammatory reaction caused by external stimuli, such as ultraviolet rays, fine dust, etc., senescence-induced attenuation of the epidermis, etc.

Accordingly, as used herein, the term "alleviation" refers to all actions that cause relief from a condition in which the skin barrier function is deteriorated or damaged, a condition in which the skin barrier function is likely to be deteriorated or damaged, and a condition that needs to prevent the above conditions, but is not limited thereto. More specifically, the alleviation activates the autophagy of epidermal keratinocytes, which is reduced by external stimuli or aging, to induce differentiation of the epidermis and accelerate the turnover of the epidermis, and thus may include all actions leading to the recovery of the barrier function of the epidermis and the prevention of aging, but is not limited thereto.

As used herein, the term "turnover" refers to a process in which new cells made in the dermal layer come up to the stratum corneum and become dead cells to fall off, and new cells are born again in the basal layer. Although it depends on the region or age, the turnover period of the epidermis in normal skin may be 4 to 6 weeks, but is not limited thereto. In the case of the composition of the present invention, the turnover of the epidermis may be promoted by activating the autophagy of epidermal keratinocytes, and the skin barrier dysfunction can be alleviated by promoting the turnover of the epidermis.

As used herein, the "cosmetic composition" may be prepared in the form selected from the group consisting of a solution, ointment for external use, cream, foam, nutritive cosmetic water, softening cosmetic water, pack, softening water, milky lotion, makeup base, essence, liquid washing agent, bath foam, sunscreen cream, sun oil, suspension, emulsion, paste, gel, lotion, powder, soap, surfactant-containing cleanser, oil, powder foundation, emulsion foundation, wax foundation, patch, and spray, but is not limited thereto. Specifically, the cosmetic composition of the present invention may be preferably prepared in a semi-solid formulation such as an ointment for external use, lotion, etc., but is not limited thereto.

Additionally, the cosmetic composition of the present invention may further include one or more cosmetically acceptable carrier mixed with a general skin cosmetic composition. As common ingredients, for example, oil, water, surfactants, moisturizers, lower alcohols, thickening agents, chelating agents, colorings, preservatives, fragrances, etc. may be appropriately mixed, but the ingredients are not limited thereto. The cosmetically acceptable carrier included in the cosmetic composition of the present invention may vary depending on the formulations.

When the formulation of the present invention is an ointment, paste, cream, or gel, animal oil, vegetable oil, wax, paraffin, starch, tragacanth, cellulose derivatives, polyethylene glycol, silicone, bentonite, silica, talc, zinc oxide, etc. may be used as a carrier ingredient, but the present invention is not limited thereto. These may be used alone or in a combination of two or more thereof.

When the formulation of the present invention is a powder or spray, lactose, talc, silica, aluminum hydroxide, calcium silicate, polyamide powder, etc. may be used as a carrier ingredient, and in particular, when it is a spray, a propellant such as chlorofluorohydrocarbon, propane/butane, or dimethyl ether may be additionally included, but the present invention is not limited thereto. These may be used alone or in a combination of two or more thereof.

When the formulation of the present invention is a solution or emulsion, solvents, solubilizing agents, or emulsifying agents may be used as a carrier ingredient, and for example, water, ethanol, isopropanol, ethyl carbonate, ethyl acetate, benzyl alcohol, benzyl benzoate, propylene glycol, 1,3-butyl glycol oil, etc. may be used. In particular, cottonseed oil, peanut oil, maize germ oil, olive oil, castor oil and sesame seed oil, glycerol aliphatic ester, polyethylene glycol, or aliphatic ester of sorbitan may be used, but the present invention is not limited thereto. These may be used alone or in a combination of two or more thereof.

When the formulation of the present invention is a suspension, liquid diluents (e.g., water, ethanol, or propylene glycol), suspending agents (e.g., ethoxylated isostearyl alcohol, polyoxyethylene sorbitol ester, and polyoxyethylene sorbitan ester), microcrystalline cellulose, aluminum metahydroxide, bentonite, agar, or tragacanth, etc. may be used as a carrier ingredient, but the present invention is not limited thereto. These may be used alone or in a combination of two or more thereof.

When the formulation of the present invention is a soap, alkali metal salts of fatty acids, fatty acid hemiester salts, fatty acid protein hydrolysates, isethionate, lanolin derivatives, aliphatic alcohols, vegetable oil, glycerol, glucose, etc. may be used as a carrier ingredient, but the present invention is not limited thereto. These may be used alone or in a combination of two or more thereof.

In the cosmetic composition of the present invention, one or more compounds selected from the group consisting of hydroxycinnamic acid, isoamyl acetate, and betaine, or an acceptable salt thereof, may preferably be contained in an amount of 0.0001% to 10% by weight based on the weight of the total cosmetic composition, and more preferably be contained in an amount of 0.0005% to 10% by weight based on the weight of the total cosmetic composition, but the present invention is not limited thereto.

The one or more compounds selected from the group consisting of hydroxycinnamic acid, isoamyl acetate, and betaine included in the cosmetic composition, or an acceptable salt thereof, may induce epidermal differentiation.

In the case of the cosmetic composition, the differentiation of the epidermis may be induced or promoted by promoting autophagy of keratinocytes, thereby improving the function of the skin barrier.

As used herein, the term "epidermis" refers to the epithelial tissue of the skin covering the surface of an animal body, and is always in contact with the external environment and thus protects the human body mainly from external physical damage and chemical substances, prevents bacteria, fungi, and viruses, etc. from invading the skin, and has a role as a protective barrier against moisture loss.

As used herein, the term "epidermal differentiation" refers to a process in which the epidermal cells present at the outermost part of the skin structure undergo the four-step process of basal cells, prickle cells, granular cells, and keratinocytes, and is a process involving changes in each cell cycle and significant changes in cell shape as various proteins are expressed in time due to gene expression changes. In the case of the cosmetic composition, the skin barrier function may be generated or maintained, or the skin barrier dysfunction may be alleviated by inducing or promoting the differentiation of epidermis.

The one or more compounds selected from the group consisting of hydroxycinnamic acid, isoamyl acetate, and betaine included in the cosmetic composition, or an acceptable salt thereof, may promote autophagy of keratinocytes.

As used herein, the term "keratinocyte" refers to a cell that divides into the main constituent cells of the epidermis and begins differentiating while moving upward, and refers to a cell that has a role in creating a skin barrier by division and differentiation through the final differentiation process.

The one or more compounds selected from the group consisting of hydroxycinnamic acid, isoamyl acetate, and betaine included in the cosmetic composition, or an acceptable salt thereof, may increase the amount of LC3. In addition, the cosmetic composition may increase the amount of LC3-I or LC3-II.

The one or more compounds selected from the group consisting of hydroxycinnamic acid, isoamyl acetate, and betaine included in the cosmetic composition, or an acceptable salt thereof, may promote autophagy in keratinocytes independently of the mTOR pathway.

The activity of autophagy is promoted to increase the production of LC3-II protein, and consequently, the skin barrier dysfunction may be alleviated and the senescence-induced attenuation of the epidermis prevented.

As used herein, the term "autophagy" is a mechanism by which damaged substances are removed or energy is regenerated by degradation of old or damaged intracellular substances and organelles when intracellular stress factor is excessively generated or an intracellular energy source is depleted, and autophagic activity is observed in the epidermis as well as in several epithelial tissues. Autophagy is essential for maintaining homeostasis of the epidermis and exerting appropriate skin barrier function. In particular, it has an important role in a viral infection of the epidermis, inflammatory reaction due to ultraviolet rays, melanosome delivery, and differentiation of keratinocytes, and also has a crucial role in removing mitochondria, Golgi apparatus, vesicles, nuclei, etc. when the keratinocytes finally differentiate into the stratum corneum. As aging progresses or accelerates, it has been reported that the intracellular autophagic activity decreases rapidly. If autophagy is suppressed, aged mitochondria or proteins with denatured structures accumulate excessively in the cell, leading to an increase in intracellular free radicals and oxidative stress, thereby increasing cell death and accelerating aging.

The autophagy may occur through lysosomes.

In one embodiment of the present invention, in order to confirm that the promotion of the synthesis of autophagosomes by betaine does not occur due to a functional defect in the lysosomes, betaine was treated together with a lysosomal activity inhibitor. As a result, it was confirmed that the degradation of autophagosomes formed by betaine occur through lysosomes.

As used herein, the terms "Light Chain 3 (LC3)", "microtubule-associated proteins", and "microtubule-associated proteins 1A/1B light chain 3B" refer to proteins whose amount increases during autophagy. They undergo a post-translational transformation process during the autophagy process. After translation into pro-LC3, they produce cytoplasmic LC3-I through cleavage of the $22^{nd}$ amino acid at the carboxy terminal by autophagy-related protein 4 (atg4), and during autophagy, LC3-I is converted to LC3-II, while being lipidated by phosphatidylethanolamine (PE) through a ubiquitin-like system involving atg3 and atg7, and consequently, LC3 is linked to autophagosomes.

In an experimental example of the present invention, when HaCaT cells were treated with betaine at different concentrations, it was confirmed that the amount of LC3-II increased as the concentration increased, and the amount of LC3-II increased dependently of the treatment time, thereby confirming that conversion mostly occurred after 24 hours. From these results, it was confirmed that the effect of promoting autophagy of keratinocytes by way of betaine can improve the barrier function of the epidermis by promoting the differentiation of the epidermis and accelerating the turnover of the epidermis.

As used herein, the term "p62" or "sequestosome 1 (SQSTM1)" is a protein that is degraded as autophagy occurs, and has a ubiquitin binding site, so that it can bind to a ubiquitinated protein. Therefore, it is possible to form a ubiquitinated protein—p62 oligomer complex and bind to LC3, which binds to autophagosomes, so that proteins and organelles in the autophagosomes including p62 can be degraded in the lysosomes. The p62 is a protein that is degraded by autophagy, and in one embodiment of the present invention, it was confirmed through the decrease in p62 (SQSTM1) protein that the substrate degradation by lysosomes is normally occurring as a degradation process through autophagy of betaine.

As used herein, the term "mammalian target of rapamycin (mTOR)" is a ser/thr kinase, which responds to changes in ATP and amino acids, and is known to have a role in balancing the availability of nutrients and cell growth. In an environment where sufficient nutrients can be supplied, mTOR is phosphorylated through the class I PI3K/Akt signaling pathway and then transmits a positive signal to the p70S6 kinase, and is involved in the inactivation of 4E-BP1, an eIF4E inhibitor, to translate specific mRNA groups, and also inhibits autophagy.

In one Experimental Example of the present invention, in order to find a mechanism by which autophagy is promoted by betaine and to identify a related upstream signal regulatory factor, the degree of phosphorylation of the AKT-mTOR-S6 pathway was measured after treating HaCaT cells with betaine. As a result, no significant difference in the mTOR signals due to betaine treatment was observed in HaCaT cells, and from this result, it was confirmed that the promotion of autophagy in keratinocytes by way of betaine occurred independently of the mTOR signals.

One or more compounds selected from the group consisting of hydroxycinnamic acid, isoamyl acetate, and betaine included in the cosmetic composition, or an acceptable salt thereof, can promote autophagy in tissues within the epidermis, and accordingly, the thickness of the epidermis can be increased, thereby improving the barrier function and preventing the senescence-induced attenuation of the epidermis. The increase in the thickness of the epidermis may be used interchangeably with the term "keratinization".

As used herein, the term "keratinization" may mean that the stratum corneum is formed as the final stage of differentiation of the epidermis.

In one Experimental Example of the present invention, the degree of LC3-II production and the increase in epidermal thickness due to treatment with hydroxycinnamic acid, isoamyl acetate, and betaine at different concentrations were confirmed in an artificial skin model. As a result, it was confirmed that the autophagy increased due to the increase in the degree of LC3-II production. Additionally, when the artificial skin tissue was stained to measure the change in the thickness of the epidermis, it was confirmed that the epidermal thickness increased by 19% compared to the control group by way of 1% betaine treatment; 42% compared to the control group by way of treatment with 1% hydroxycinnamic acid; and by 37% compared to the control group by way of treatment with 1% isoamyl acetate. From these results, it was confirmed that hydroxycinnamic acid, isoamyl acetate, and betaine can promote autophagy of keratinocytes and also improve the barrier function of the epidermis by inducing the differentiation of the epidermis and accelerating the turnover of the epidermis (see Experimental Example 5 and FIGS. 5a, 5b, 5c, and 5d).

In order to achieve the objects above, another aspect of the present invention provides a method for alleviating skin barrier dysfunction, including applying the cosmetic composition to the skin of a subject. The cosmetic composition, the skin barrier function, the skin barrier dysfunction, and the alleviation are as described above.

As used herein, the term "subject" refers to all animals as well as mammals, including mice, livestock, and humans, but is not limited thereto. In addition, as used herein, the term "application" means bringing the composition of the present invention into contact with the skin of a subject by any suitable method, and may include all actions aimed at absorption of the composition into the skin through application, but is not limited thereto.

In order to achieve the objects above, still another aspect of the present invention provides a pharmaceutical composition for preventing or treating skin barrier dysfunction, including one or more compounds selected from the group consisting of hydroxycinnamic acid, isoamyl acetate, and betaine, or a pharmaceutically acceptable salt thereof, as an active ingredient. The pharmaceutical composition may include a combination of two or more compounds selected from the group consisting of hydroxycinnamic acid, isoamyl acetate, and betaine, but is not limited thereto. The hydroxycinnamic acid, the isoamyl acetate, the betaine, the skin barrier function, and the skin barrier dysfunction are as described above.

As used herein, the term "prevention" refers to all actions that suppress or delay the skin barrier dysfunction by administering the pharmaceutical composition to a subject or applying the pharmaceutical composition onto the skin of a subject.

As used herein, the term "treatment" refers to all actions that alleviate or beneficially change the symptoms of skin barrier dysfunction by administering the pharmaceutical composition to a subject or applying the pharmaceutical composition onto the skin of a subject.

The pharmaceutical composition may treat or prevent an inflammatory reaction caused by external stimuli, such as ultraviolet rays, fine dust, etc., senescence-induced attenuation of the epidermis, etc., which constitute skin barrier dysfunction. Additionally, skin diseases caused by the skin barrier dysfunction may be prevented or treated.

The skin disease is a disease that affects the skin system, and the skin system includes the entire surface of the human body, and may include the skin, hair, nails, and related muscles and glands.

The skin disease may be, for example, atopic dermatitis, xeroderma, psoriasis, ichthyosis, contact dermatitis, lichen planus, pityriasis, eczema, ichthyosis, acne, etc., but the skin disease is not limited thereto.

As used herein, the term "pharmaceutical composition" may further include appropriate carriers, excipients, and diluents which are commonly used in the preparation of pharmaceutical compositions, in addition to including one or more compounds selected from the group consisting of hydroxycinnamic acid, isoamyl acetate, and betaine, or a pharmaceutically acceptable salt thereof, as an active ingredient.

Specifically, the pharmaceutical composition may be formulated according to common methods into oral dosage forms (e.g., powders, granules, tablets, capsules, suspensions, emulsions, syrups, aerosols, etc.) external dosage forms, or sterile injectable solutions to be used. The carriers, excipients, and diluents which may be included in the pharmaceutical composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, etc., but are not limited thereto. These may be used alone or in a combination of two or more thereof.

When formulating the pharmaceutical composition of the present invention, it may be prepared by using a commonly used diluent or excipient, such as a filler, an extender, a binder, a wetting agent, a disintegrant, a surfactant, etc.

Examples of a solid formulation for oral administration include a tablet, a pill, a powder, a granule a capsule, etc. These solid formulations are prepared by mixing the pharmaceutical composition with one or more excipient, for example, starch, calcium carbonate, sucrose, lactose, gelatin, etc. A lubricant such as magnesium stearate or talc may also be used in addition to the simple excipient. Examples of a liquid formulation for oral administration include a suspension, a solution for internal use, an emulsion, a syrup, etc. The liquid formulation may include, in addition to a commonly available simple diluent (e.g., liquid paraffin or water), various excipients (e.g., a wetting agent, a sweetener, an aromatic, or a preservative), etc.

A formulation for parenteral administration may include a sterilized aqueous solution, a non-aqueous solvent, a suspension, an emulsion, a lyophilized formulation, an external preparation, etc. The non-aqueous solvent and the suspension may be propylene glycol, polyethylene glycol, a plant oil (e.g., olive oil), an injectable ester (e.g., ethyl oleate), etc.

The pharmaceutical composition of the present invention may be preferably prepared in a semi-solid formulation such as an ointment for external use, a lotion, etc., but is not limited thereto.

The pharmaceutically effective dose or the effective dosage of the pharmaceutical composition of the present invention may vary depending on the formulation methods, administration methods, dosing intervals, and/or administration routes of the pharmaceutical composition. Additionally, it may vary depending on many factors including the type and extent of reaction to be achieved by administration of the pharmaceutical composition, the type, age, weight, general health conditions, symptoms or severity of diseases, gender, diet, and excretion of target individuals for administration, ingredients of other medical composition used synchronously or asynchronously for the corresponding individual, and analogous factors well known in the medical field. Those of ordinary skill in the corresponding technical field can easily determine and prescribe the effective dosage for the intended treatment.

The pharmaceutical composition of the present invention may be administered in a single or multiple divided doses per day. Accordingly, the dosage does not limit the scope of the present invention in any aspect.

The administration route and administration method of the pharmaceutical composition of the present invention may each be independent, and are not particularly limited. Additionally, as long as the pharmaceutical composition can be delivered to a target tissue, it can be administered by any administration route and administration method. The pharmaceutical composition can be administered orally or parenterally, and may be preferably administered parenterally.

As the parenteral administration method, for example, intravenous administration, intraperitoneal administration, intramuscular administration, transdermal administration, subcutaneous administration, etc. may be used, and methods of applying, spraying, or inhaling the composition to a diseased area may also be used, but the present invention is not limited thereto.

The pharmaceutical composition of the present invention may be more preferably administered by transdermal administration during parenteral administration, and more preferably by a topical application method including applying the pharmaceutical composition to the skin of a subject.

In order to achieve the objects above, still another aspect of the present invention provides a method for preventing or treating skin barrier dysfunction, including administering the pharmaceutical composition to a subject excluding humans, or applying the pharmaceutical composition to the skin of a subject excluding humans. The pharmaceutical composition, the skin barrier function, the skin barrier dysfunction, the prevention, and the treatment are as described above. In addition, the subject and the application are also as described above.

In order to achieve the objects above, still another aspect of the present invention provides a quasi-drug composition for preventing or alleviating skin barrier dysfunction, which includes one or more compounds selected from the group consisting of hydroxycinnamic acid, isoamyl acetate, and betaine, or a pharmaceutically acceptable salt thereof, as an active ingredient. The quasi-drug composition may include a combination of two or more compounds selected from the group consisting of hydroxycinnamic acid, isoamyl acetate, and betaine, but is not limited thereto. The quasi-drug composition, the skin barrier function, the skin barrier dysfunction, the prevention, and the treatment are as described above.

As used herein, the "quasi-drug composition" may further include a pharmaceutically acceptable carrier, excipient, or diluent, if necessary, in addition to including one or more compounds selected from the group consisting of hydroxycinnamic acid, isoamyl acetate, and betaine, or a pharmaceutically acceptable salt thereof, as an active ingredient. The pharmaceutically acceptable carrier, the excipient, or the diluent is not limited as long as it does not impair the effect of the present invention and may include, for example, a filler, an extender, a binder, a wetting agent, a disintegrant, a surfactant, a lubricant, a sweetener, an aromatic, a preservative, etc.

The quasi-drug composition of the present invention may include a disinfectant cleaner, a shower foam, an ointment, a wet tissue, a coating agent, etc., and may preferably be prepared in a semi-solid formulation such as an ointment for external use, a lotion, etc., but is not limited thereto. The formulation methods, dosages, methods of use, components, etc. of the quasi-drug may be appropriately selected from conventional techniques known in the art.

Mode for Carrying Out the Invention

Hereinafter, the configuration and effect of the present invention will be described by way of Examples and Experimental Examples. However, these Examples and Experimental Examples are provided for illustrative purposes only, and the scope of the invention is not intended to be limited by these Examples and Experimental Examples.

EXAMPLE 1

Reagents and Devices

Betaine (Sigma, USA) was dissolved in DMSO to be used in the experiments. Bafilomycin A1 (b1793), which is a selective inhibitor of lysosome activity used in the experiments, was purchased from Sigma-Aldrich (USA). AKT (9272S), p-AKT (ser473) (9271S), p-S6 (ser240/244) (2215), and S6 (2217), which are primary antibodies, were purchased from Cell Signaling Technology (USA); LC3B (NB100-2220) was purchased from Novus Biologicals (USA); and p62 SQSTM1 (D-3) (sc-28359) and α-Tubulin (sc-8035) were purchased from Santa Cruz Biotechnology to be used in the experiments.

EXAMPLE 2

Culture of Epidermal Cells

Human skin-derived keratinocytes (NHEK-Neo, Neonatal Normal Human Epidermal Keratinocytes) used in this experiment were purchased from Lonza (192907, USA), and were cultured in a culture medium prepared by adding 10% fetal bovine serum (FBS), 50 U/mL penicillin, and 50 µg/mL streptomycin to a KGM-Gold medium (Lonza, USA). Human keratinocyte cell line (HaCaT) was cultured in a DMEM medium (Gibco, USA) containing 10% fetal bovine serum (FBS), 50 U/mL penicillin, 50 µg/mL streptomycin, and 0.01 mM $CaCl_2$ at 37° C. and 5% $CO_2$. When the cells grew up to 70% to 80% of the culture flask, they were subcultured.

EXAMPLE 3

Introduction of GFP-LC3 Vector and Quantification of LC3 Puncta

A GFP (green fluorescence protein)-conjugated microtubule-binding protein 1 light chain 3 (LC3) expression vector (Cell Biolabs, USA) was introduced into HaCaT cells using Lipofectamine 2000 (Invitrogen, USA), which is a gene transfer reagent, and the resultant was cultured for 12 hours in a condition containing 10% FBS and then treated with candidate compounds expected to promote autophagy, which was selected from a library of single compounds derived from natural substances, at each concentration in the medium. Subsequently, the evaluation was performed by fluorescence microscopy (Leica Microsystems, USA). In order to quantify the induction of autophagy, 100 GFP-positive cells in which puncta autophagosomes were formed (punctae=5) were counted using fluorescence microscopy.

EXAMPLE 4

Western Blotting Analysis

HaCaT cells were inoculated into a 60 mm plate at a concentration of $8\times10^5$ cells and independently treated with hydroxycinnamic acid, isoamyl acetate, and betaine the next day, and then the cells were eluted with a 5× lysis buffer to obtain proteins. Cell debris was removed by centrifugation and quantified using a BCA protein assay kit (Pierce, USA). The cell-extracted proteins were isolated using a 4%-15% SDS-PAGE gel (Bio-Rad, USA) and transferred to a nitrocellulose membrane (Life Technologies, New Zealand). The cells were then blocked with a TBST buffer containing 3% BSA for 1 hour and thereupon reacted in a buffer solution containing primary antibodies at 4° C. for 1 day. The membrane was washed with TBST, reacted with peroxidase-conjugated secondary antibodies, and then colored using enhanced chemiluminescence (Amersham, UK), and the immune-reactive bands were confirmed with the Fusion FX 5 image system (Vilber Lourmat, France).

EXAMPLE 5

Culture of 3D Artificial Skin Tissue

A reconstructed human epidermis model (Neoderm-E, Tego Science, Korea) was transferred to a 6-well plate and stabilized in 2 mL of a growth medium (Tego Science, Korea) for 24 hours, and the cream-type hydroxycinnamic acid, isoamyl acetate, and betaine were applied to the artificial skin at each concentration. After culturing for 24 hours, the hydroxycinnamic acid, isoamyl acetate, and betaine cream applied on the artificial skin were washed with phosphate buffer saline (PBS), and then the tissue was disrupted using a RIPA buffer (50 mM Tris-HCl, pH 7.4, 150 mM NaCl, 1% NP-40) containing Protease Inhibitor Cocktails (ThermoFisher Scientific, USA) by sonication. The tissue-extracted proteins were analyzed for the autophagic activity of keratinocytes in the tissue by western blotting analysis. 1% creams of hydroxycinnamic acid, isoamyl acetate, and betaine were applied on the artificial skin, followed by H&E staining after 1 week to confirm the increase in thickness of the epidermis.

EXAMPLE 6

Statistical Analysis

Statistical significance for the difference in the experimental results was evaluated by an independent analysis of variance, and probability values were calculated by an independent t-test. If the p value was less than 0.05, it was judged to be statistically significant.

EXPERIMENTAL EXAMPLE 1

Screening for Autophagy-Activating Materials in Keratinocytes

In order to improve the barrier function by promoting epidermal differentiation through the activation of autophagy, which is reduced due to aging or external stimuli, a search was conducted starting from a library of single compounds derived from natural substances for those that promote autophagic activity of keratinocytes. Specifically, as in the method of Example 3, candidate compounds expected to promote autophagy were treated to HaCaT cells introduced with the GFP-LC3 vector. Thereafter, the number of cells with increased GFP-LC3 puncta vesicles in the cytoplasm was increased as GFP was conjugated to LC3, which was converted into a membrane-bound form when autophagy was induced in each cell, was compared. As a result, upon treatment with the hydroxycinnamic acid, isoamyl acetate, and betaine, the proportion of cells with increased GFP-LC3 puncta vesicles were 20.8%, 16.4%, and 25%, respectively (it was confirmed that the number of cells with increased GFP-LC3 puncta vesicles was increased by 18.75% compared to the untreated group upon treatment with betaine). From these results, it can be confirmed that hydroxycinnamic acid, isoamyl acetate, and betaine can be used as compound materials for activation of autophagy in keratinocytes.

EXPERIMENTAL EXAMPLE 2

Confirmation of Cytotoxicity of Betaine on Keratinocytes and Efficacy of Promoting Autophagy in Keratinocytes The cytotoxicity of betaine on keratinocytes was confirmed, and the results of Experimental Example 1 were confirmed by the western blotting analysis of Example 4 to determine the degree of production of LC3-II converted as it entered into the double membranes of the autophagosomes. As a result, when each of 10 µg/mL, 50 µg/mL, and 100 µg/mL betaine was treated to the HaCaT cells, no cytotoxicity was observed at any concentration (FIG. 2A). Subsequently, when betaine was treated at the same concentration as in the above experiment, it was confirmed that the amount of LC3-II increased as the concentration increased (FIG. 2B). Additionally, the cells were treated with 50 µg/mL betaine and the amount of LC3-II conversion per hour was observed. As a result, although a significant increase was not observed until 6 hours, the amount of conversion increased from 12 hours, and the highest conversion was observed after 24 hours.

From these results, the effect of promoting autophagy of keratinocytes by betaine increases depending on the concentration and time of betaine treatment, and the barrier function of the epidermis can be improved by promoting the differentiation of the epidermis and accelerating the turnover of the epidermis.

EXPERIMENTAL EXAMPLE 3

Confirmation of Promotion of Autophagosome Synthesis by Betaine

The increase of intracellular autophagosomes can largely have two causes: 1) activation of various signaling processes related to the production of autophagosomes, or 2) the autophagosomes ultimately binding with lysosomes to degrade the proteins in the vesicles and being recycled. However, the autophagosomes may accumulate due to a problem in the degradation process due to a functional defect in the lysosomes.

Therefore, in order to investigate a mechanism by which the autophagosomes are increased by way of betaine treatment, the cells were treated with bafilomycin A1 (Baf. A1), which is known as a lysosomal activity inhibitor, together with betaine, and the degree of LC3-II production was confirmed by western blotting analysis. As a result, it was observed that the amount of LC3-II further increased when bafilomycin A1 was treated together with betaine compared to when betaine was treated alone, thereby confirming that the degradation of autophagosomes formed due to betaine occur normally through lysosomes (FIG. 3). Additionally, by confirming that the amount of p62/SQSTM1 (p62) protein, which is known to be degraded by autophagy, was also reduced by way of the treatment of betaine, it was confirmed that the substrate degradation by the lysosomes was proceeding normally. From these results, it was confirmed that the promotion of autophagy by way of betaine was not due to stagnation of degradation of autophagy, but due to activation of various signaling processes related to autophagy.

EXPERIMENTAL EXAMPLE 4

Confirmation of Mechanism of mTOR Pathway—Independent Autophagic Activity

In previous studies, betaine—homocysteine methyltransferase (BHMT) has been reported to reduce the amount of homocysteine in a betaine-dependent manner. In one study, homocysteine was reported to promote the activity of mTORC1, an enzyme that inhibits autophagy. Thus, in order to find a mechanism by which autophagy is promoted by betaine, an experiment was conducted to identify related upstream signaling factors. Specifically, in order to observe whether the activity of mTORC1 is regulated by way of betaine treatment, the degree of phosphorylation of the AKT-mTOR-S6 pathway was confirmed by western blotting analysis after treating the HaCaT cell line with betaine.

As a result, it was not possible to observe a significant difference in the mTOR signals by betaine treatment in the HaCaT cells, and it was confirmed therefrom that the promotion of autophagy in keratinocytes by betaine occurred independently of the mTOR signals (FIG. 4).

EXPERIMENTAL EXAMPLE 5

Confirmation of Effects of Promoting Differentiation in Epidermis and Increasing Epidermal Thickness in 3D Artificial Skin Model In order to confirm whether the differentiation in the epidermis is promoted by the effect of promoting autophagy by way of betaine, hydroxycinnamic acid, and isoamyl acetate, a 3D artificial skin model was used as in Example 5. Cream formulations of 1% betaine, 3% betaine, 5% betaine, 0.1% hydroxycinnamic acid, 0.5% hydroxycinnamic acid, 1% hydroxycinnamic acid, 0.1% isoamyl acetate, 0.5% isoamyl acetate, and 1% isoamyl acetate were prepared and applied onto the keratinocytes. After 24 hours, the degree of LC3-II production was measured through western blotting analysis to determine whether autophagy in the epidermis was promoted.

As a result of the experiment, autophagy was increased by treatment with 1% betaine, 1% hydroxycinnamic acid, and 1% isoamyl acetate (see FIGS. 5A, 5B, and 5C, respectively). Next, the cream formulations of 1% betaine, 1% hydroxycinnamic acid, and 1% isoamyl acetate were applied to the artificial skin, and changes in the thickness of the epidermis were measured after Fontana-Masson staining of the artificial skin tissue. As a result, as can be seen from Table 1 and FIG. 5D, the epidermal thickness was increased by 19% as a result of treatment with 1% betaine compared to the control group; the epidermal thickness was increased by 42% as a result of treatment with 1% hydroxycinnamic acid compared to the control group; and the epidermal thickness was increased by 37% as a result of treatment with 1% isoamyl acetate compared to the control group.

TABLE 1

|  | Thickness of Epidermis (μm) | S.D. | Increase relative to Control |
| --- | --- | --- | --- |
| Control | 62 | 4.26 | 1.00 |
| betaine | 74 | 4.78 | 1.19 |
| hydroxycinnamic acid | 88 | 4.36 | 1.42 |
| isoamyl acetate | 85 | 4.11 | 1.37 |

From these results, it was confirmed that betaine, hydroxycinnamic acid, and isoamyl acetate can promote the autophagy of keratinocytes, and can improve the barrier function of the epidermis by inducing the differentiation of the epidermis and by accelerating the turnover of the epidermis.

Those of ordinary skill in the art will recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. A method for alleviating skin barrier dysfunction, comprising
   applying a cosmetic composition to the skin of a subject in need thereof,
   wherein the cosmetic composition comprises one or more compositions selected from the group consisting of hydroxycinnamic acid, isoamyl acetate, and an acceptable salt thereof, as an active ingredient,
   wherein the skin barrier dysfunction is any one or more selected from the group consisting of decrease in epidermal thickness, attenuation of turnover of the epidermis, and xerosis,
   wherein alleviation of the skin barrier dysfunction is achieved by promoting autophagy of keratinocytes, and
   wherein the autophagy is not dependent on a mammalian target of rapamycin (mTOR) pathway.

2. A method for treating skin barrier dysfunction, comprising
   administering a pharmaceutical composition to a subject in need thereof, or applying the pharmaceutical composition to a skin of a subject in need thereof,
   wherein the pharmaceutical composition comprises one or more compositions selected from the group consisting of hydroxycinnamic acid, isoamyl acetate, and a pharmaceutically acceptable salt thereof, as an active ingredient,
   wherein the skin barrier dysfunction is any one or more selected from the group consisting of decrease in epidermal thickness, attenuation of turnover of the epidermis, and xerosis,
   wherein treatment of the skin barrier dysfunction is achieved by promoting autophagy of keratinocytes, and
   wherein the autophagy is not dependent on a mammalian target of rapamycin (mTOR) pathway.

3. The method of claim 1, wherein the hydroxycinnamic acid and isoamyl acetate or an acceptable salt thereof, are each contained in an amount of 0.0001% to 10% by weight based on the total weight of the cosmetic composition.

4. The method of claim 1, wherein the cosmetic composition has a formulation selected from the group consisting of a solution, ointment for external use, cream, foam, nutritive cosmetic water, softening cosmetic water, pack, softening water, makeup base, essence, liquid washing agent, bath foam, sunscreen cream, sun oil, suspension, emulsion, paste, gel, lotion, powder, soap, surfactant-containing cleanser, oil, powder foundation, emulsion foundation, wax foundation, patch, and spray.

5. The method of claim 1, wherein the cosmetic composition increases an amount of light chain 3 (LC3).

6. The method of claim 1, wherein the alleviation of the skin barrier dysfunction is achieved by increasing a thickness of skin epidermis.

* * * * *